US012725699B2

(12) United States Patent
Blasberg et al.

(10) Patent No.: US 12,725,699 B2
(45) **Date of Patent: *Sep. 1, 2026**

(54) HOME DIALYSIS MACHINE NETWORK INCLUDING WALK-UP SERVICE CENTERS

(71) Applicants: Fresenius Medical Care Holdings, Inc., Waltham, MA (US); Fresenius Medical Care AG, Bad Homburg (DE)

(72) Inventors: Stacy L. Blasberg, Needham, MA (US); Zdenek Cerman, Bad Homburg (DE)

(73) Assignees: FRESENIUS MEDICAL CARE HOLDINGS, INC., Waltham, MA (US); FRESENIUS MEDICAL CARE AG, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,486

(22) Filed: Apr. 18, 2024

(65) Prior Publication Data

US 2024/0266039 A1 Aug. 8, 2024

Related U.S. Application Data

(63) Continuation of application No. 17/232,660, filed on Apr. 16, 2021, now Pat. No. 11,996,187.
(Continued)

(51) Int. Cl.
*G16H 40/40* (2018.01)
*A61M 1/16* (2006.01)
(Continued)

(52) U.S. Cl.
CPC .......... *G16H 40/40* (2018.01); *A61M 1/1654* (2013.01); *G05B 23/0267* (2013.01);
(Continued)

(58) Field of Classification Search
CPC .................................................. A61M 1/1654
(Continued)

(56) References Cited

U.S. PATENT DOCUMENTS 8,057,679 B2 11/2011 Yu et al.
9,827,680 B2 11/2017 Davey et al.
(Continued)

FOREIGN PATENT DOCUMENTS

EP 3495005 B1 1/2021
JP 2001346870 A 12/2001
(Continued)

OTHER PUBLICATIONS

Cvshealth, Transforming the Consumer Health Care Experience, printed Feb. 25, 2020 (27 pages).
(Continued)

*Primary Examiner* — Reginald R Reyes
(74) *Attorney, Agent, or Firm* — Kilyk & Bowersox, P.L.L.C.

(57) ABSTRACT

A home dialysis machine network is provided that includes a home dialysis machine and one or more walk-up service centers. The walk-up service center can be equipped with a diagnostic tool, parts, or supplies for the home dialysis machine. Methods of maintaining a home dialysis machine are also provided as are service centers equipped with a transportation service or office, a diagnostics department, an education and training department, a consultation department, an exercise and spa department, an entertainment department, a sales department, a repair shop, a new technologies department, a pharmacy, and a doctor's office.

18 Claims, 2 Drawing Sheets

Related U.S. Application Data

(60) Provisional application No. 63/025,518, filed on May 15, 2020.

(51) Int. Cl.

| | |
|---|---|
| ***G05B 23/02*** | (2006.01) |
| ***G06Q 10/087*** | (2023.01) |
| ***G06Q 10/20*** | (2023.01) |
| ***G06Q 30/012*** | (2023.01) |
| ***G06Q 40/08*** | (2012.01) |
| ***G09B 19/00*** | (2006.01) |
| ***G16H 10/60*** | (2018.01) |
| ***G16H 20/10*** | (2018.01) |
| ***G16H 20/40*** | (2018.01) |
| ***G16H 40/20*** | (2018.01) |
| ***G16H 40/67*** | (2018.01) |
| ***G16H 50/20*** | (2018.01) |
| ***G16H 80/00*** | (2018.01) |
| ***H04L 67/12*** | (2022.01) |
| *G16H 70/20* | (2018.01) |

(52) U.S. Cl.

CPC ........... *G06Q 10/087* (2013.01); *G06Q 10/20* (2013.01); *G06Q 30/012* (2013.01); *G06Q 40/08* (2013.01); *G09B 19/0092* (2013.01); *G16H 10/60* (2018.01); *G16H 20/10* (2018.01); *G16H 20/40* (2018.01); *G16H 40/20* (2018.01); *G16H 40/67* (2018.01); *G16H 50/20* (2018.01); *G16H 80/00* (2018.01); *H04L 67/12* (2013.01); *G16H 70/20* (2018.01)

(58) Field of Classification Search

USPC .......................................................... 702/183

See application file for complete search history.

(56) References Cited

U.S. PATENT DOCUMENTS

| | | | |
|---|---|---|---|
| 10,350,343 B2 | 7/2019 | Minkus | |
| 10,740,437 B1 | 8/2020 | Shannon et al. | |
| 10,758,660 B2 | 9/2020 | Leinfellner et al. | |
| 11,229,727 B2 | 1/2022 | Tatonetti | |
| 11,357,896 B2 | 6/2022 | Leinfellner et al. | |
| 2005/0240613 A1 | 10/2005 | Logan, Jr. | |
| 2012/0138533 A1 | 6/2012 | Curtis et al. | |
| 2013/0292407 A1 | 11/2013 | Beavis et al. | |
| 2013/0310726 A1 | 11/2013 | Miller et al. | |
| 2014/0230071 A1 | 8/2014 | Adam et al. | |
| 2014/0276375 A1 | 9/2014 | Minkus | |
| 2014/0288947 A1 | 9/2014 | Simpson et al. | |
| 2015/0025499 A1 | 1/2015 | Trock et al. | |
| 2017/0011175 A1 | 1/2017 | Cocks et al. | |
| 2017/0024531 A1 | 1/2017 | Malaviya | |
| 2018/0308573 A1 | 10/2018 | Hochrein et al. | |
| 2019/0015013 A1 | 1/2019 | Zhu et al. | |
| 2019/0111200 A1 | 4/2019 | Maheshwari et al. | |
| 2019/0348160 A1 | 11/2019 | Heavelyn et al. | |
| 2019/0365976 A1* | 12/2019 | Tatonetti | A61M 1/1613 |
| 2020/0051674 A1 | 2/2020 | Long et al. | |
| 2021/0358608 A1* | 11/2021 | Blasberg | G16H 20/40 |
| 2022/0062518 A1 | 3/2022 | Tatonetti | |

FOREIGN PATENT DOCUMENTS

| | | |
|---|---|---|
| JP | 2002024382 A | 1/2002 |
| JP | 5404137 B2 | 1/2014 |
| JP | 2014-193377 A | 10/2014 |
| WO | 2020006390 A1 | 1/2020 |

OTHER PUBLICATIONS

Cvshealth, Health Trends Report 2020, printed Mar. 23, 2021 (16 pages).

Anonymous: "Medicare Benefit Policy Manual. Chapter 11—End Stage Renal Disease (ESRD). Rev. 257", Medicare Benefit Policy Manual, Jan. 3, 2019 (Jan. 3, 2019), XP055822486, Retrieved from the Internet: URL:https://web.archive.org/web/20200117014400if_/https://www.cms.gov/Regulations-and-Guidance/Guidance/Manuals/Downloads/bp102cll.pdf [retrieved on Jul. 8, 2021].

Haroon et al.: "Haemodialysis at home: review of current dialysis machines", Expert Review of Medical Devices, UK, vol. 15, No. 5, Apr. 30, 2018, pp. 337-347.

Anonymous: "Home hemodialysis—Wikipedia", Apr. 28, 2020 (Apr. 28, 2020), XP055822957, Retrieved from the Internet: URL:https://en.wikipedia.org/w/index.php?title=Home_hemodialysis&oldid=953638293 [retrieved on Jul. 9, 2021].

Anonymous: "Health club—Wikipedia", Apr. 2, 2020 (Apr. 2, 2020), XP055822993, Retrieved from the Internet: URL: https://en.wikipedia.org/w/index.php?title=Health_club&oldid=948732124 [retrieved on Jul. 9, 2021].

Anonymous: "Kiosk (disambiguation)—Wikipedia", Sep. 6, 2019 (Sep. 6, 2019), XP055823005, Retrieved from the Internet: URL:https://en.wikipedia.org/w/index.php?title=Kiosk_(disambiguation)&oldid=914264458 [retrieved on Jul. 9, 2021].

Anonymous: "Day spa—Wikipedia", Sep. 22, 2019 (Sep. 22, 2019), XP055823006, Retrieved from the Internet: URL:https://en.wikipedia.org/w/index.php?title=Day_spa&oldid=917169149 [retrieved on Jul. 9, 2021].

Anonymous: "Telehealth—Wikipedia", May 12, 2020 (May 12, 2020), XP055823008, Retrieved from the Internet: URL: https://en.wikipedia.org/w/index.php?title=Telehealth&oldid=956302103#Videotelephony [retrieved on Jul. 9, 2021].

Anonymous: "Vehicular automation—Wikipedia", Apr. 13, 2020 (Apr. 13, 2020), XP055823012, Retrieved from the Internet: URL:https://en.wikipedia.org/w/index.php?title=Vehicular_automation&oldid=950629129 [retrieved on Jul. 9, 2021].

Anonymous: "Radio-frequency identification—Wikipedia", May 14, 2020 (May 14, 2020), XP055823017, Retrieved from the Internet: URL:https://en.wikipedia.org/w/index.php?title=Radio-frequency_identification&oldid=956577348 [retrieved on Jul. 9, 2021].

Anonymous: "Robot—Wikipedia", Apr. 20, 2020 (Apr. 20, 2020), XP055823021, Retrieved from the Internet: URL:https://en.wikipedia.org/w/index.php?title= Robot&oldid=952016237 [retrieved on Jul. 9, 2021].

Partial International Search Report (Form PCT/ISA/206 Annex) for International Patent Application No. PCT/US2021/027657, date of mailing Jul. 26, 2021, 6 pages.

Provisional Opinion Accompanying the Partial Search Report (EPO Form 1707) for International Patent Application No. PCT/US2021/027657, date of mailing Jul. 26, 2021, 19 pages.

Office Action dated Nov. 12, 2025, from Intellectual Property India for corresponding Indian Patent Application No. 202237060926.

* cited by examiner

HOME DIALYSIS MACHINE NETWORK INCLUDING WALK-UP SERVICE CENTERS

CROSS-REFERENCE TO RELATED APPLICATION

This application is a continuation of U.S. patent application Ser. No. 17/232,660, filed Apr. 16, 2021, which in-turn claims priority to U.S. Provisional Patent Application No. 63/025,518, filed May 15, 2020, both of which are incorporated herein in their entireties by reference.

FIELD OF THE INVENTION

The present invention relates to a home dialysis machine, methods of using and maintaining the same, and networks for medical equipment.

BACKGROUND OF THE INVENTION

Home dialysis machines are becoming more and more popular and practical. There is a need for better ways to use and maintain home dialysis machines. There is also a need to provide a home dialysis machine use and maintenance facility and network to ease the tasks of using, servicing, and maintaining a home dialysis machine.

SUMMARY OF THE INVENTION

The present invention provides a home dialysis machine network that includes a home dialysis machine and one or more walk-up service centers. One or more of the walk-up service centers can be equipped with a diagnostic tool, parts and supplies for the home dialysis machine, a parts and service ordering system, a centralized shipping center, a combination thereof, or the like. Many home dialysis patients can be enrolled with or use the same walk-up service center. The walk-up service center and network can teach and provide methods of maintaining a home dialysis machine. The network can include a doctor, a pharmacy, a scheduling service, a prescriptions system, methods and means to provide instructions, and the like. Each service center can be equipped with one or more of a transportation service department, a diagnostics department, an education department, a training department, a consultation department, an exercise department, a spa department, an entertainment department, a sales department, a repair shop, a new technologies department, a pharmacy, and a doctor's office. The service center can be located in an existing store or office, such as in an existing pharmacy store, drug store, grocery store, department store, or the like.

The parts and service ordering system and the shipping system can be parts of an ordering and shipping center, for example, a centralized ordering and shipping center. A home dialysis patient, care partner, or caregiver (e.g., customer) can bring a home dialysis machine into, or send a home dialysis machine to, a network walk-up service center for a diagnosis. The customer and/or walk-up service center can then use a centralized system to ship the machine, after repair, upgrade, update, or maintenance, directly to the customer's home after the diagnosis and any needed services are completed. Instead, or in addition, the customer, and/or a walk-up service center representative, can use the centralized system to order and have shipped a component, peripheral device, supplies, a software update, or a combination thereof, after the diagnosis and service are completed. In some cases, one or more items can be attended to at the walk-up service center and one or more items can be attended to remotely or at a different time. For example, a software update can be performed at the walk-up service center and a new disposable tubing set can be ordered, shipped to the customer's home, and installed by the customer or a technician. The shipping times, availabilities, and options can depend on shipping variables and the availability of requested parts, peripheral devices, disposables, consumables, software, and the like.

The walk-up service center can be configured to provide a patient, care partner, caregiver, or other customer with updates, upgrades, and patches for software, firmware, hardware, or combinations thereof, herein referred to as software, pertaining to, run by, or stored on a home dialysis machine, a peripheral therefor, the network, or the like. The software can be made available at the walk-up service center via an ordering and shipping center, an app, a downloadable app, a kiosk, a self-service kiosk, attended to by a walk-up service center representative, or the like. Before, during, or after checking for software, the walk-up service center, ordering and shipping center, app, or the like, can be configured to notify a patient, care partner, caregiver, or other customer that an update, upgrade, or patch is available for software, firmware, hardware, or combinations thereof pertaining to, run by, or stored on a home dialysis machine, a peripheral therefor, the network, or the like. The app can specify between a mandatory update, a recommended update, an optional update, and the like.

BRIEF DESCRIPTION OF THE DRAWINGS

The invention may be more fully understood with reference to the accompanying drawings. The drawings are intended to illustrate, not limit, the present teachings.

DETAILED DESCRIPTION OF THE INVENTION

Figure 1:
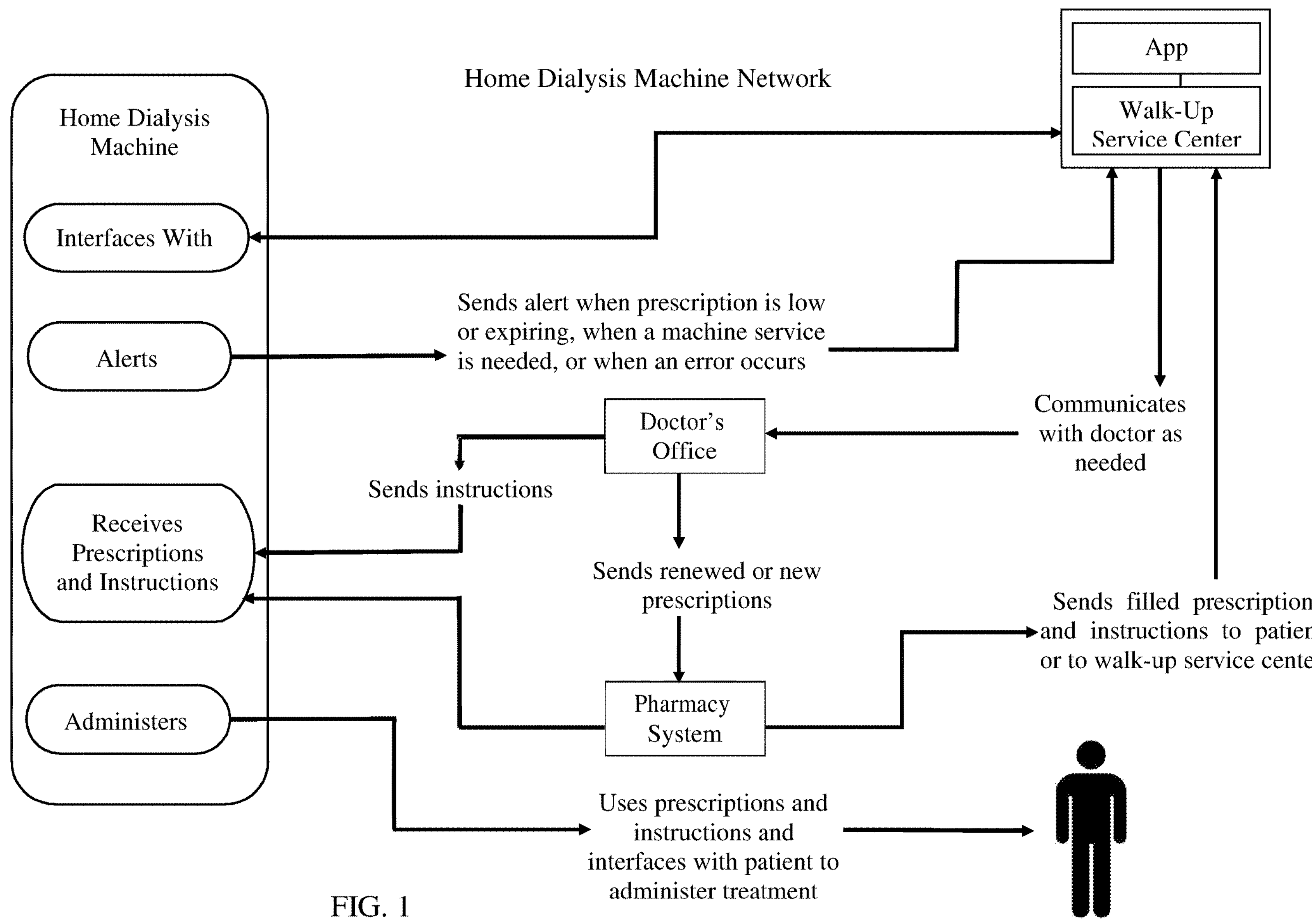
FIG. 1 is a flow diagram showing the various steps and orders that are followed according to various methods carried out by a home dialysis machine network according to an embodiment of the present invention.

According to one or more embodiments of the present invention, a network for home dialysis machines is provided. The network can comprise a home dialysis machine, one or more walk-up service centers, and a software interface, such as a website, software program, or mobile application (app) loaded on a home computer to facilitate communication between a patient or caregiver of the home dialysis machine and the one or more walk-up service centers. The walk-up service center can be equipped with a diagnostic tool configured to diagnose the home dialysis machine, a component for the home dialysis machine, a peripheral device to be used with the home dialysis machine, or a combination thereof. The diagnosis can comprise identifying at least one issue or component that is causing the machine or treatment to run with sub-optimal performance or to not run at all.

The diagnosis can comprise identifying at least one issue or component, for example, a faulty component, that is causing the machine or treatment to run with sub-optimal performance or not run at all. The diagnosis can comprise receiving values, for example, measured pressures, flow rates, conductivities, and the like, and comparing such values to threshold values, value ranges, minimum values, maximum values, combinations thereof, or the like. The diagnosis can comprise comparing received values to values stored in a local memory, stored in a look-up table, obtained from a website, or the like. The diagnosis can comprise comparing software editions stored on or run by the home dialysis machine, to recent or most recent software editions available for the home dialysis machine. The diagnosis can comprise running a second diagnostic step in response to results obtained from a first diagnostic step, for example, a second diagnostic step selected from a plurality of possible diagnostic steps.

The walk-up service center can be equipped with parts for servicing the home dialysis machine, repairing the home dialysis machine, or both. The walk-up service center can be equipped with parts for servicing or repairing a component of the home dialysis machine, a peripheral device to be used with the home dialysis machine, or a combination thereof. The walk-up service center can be equipped with supplies to be consumed before, during, or subsequent to operation of the home dialysis machine. The supplies that can be consumed during operation of the home dialysis machine can comprise at least one member selected from: disposable components; plastic components; one-time use components; a tubing set; dialysate; concentrated dialysate; powdered dialysate; packets of electrolytes formulated to mix with water to form dialysate; batteries; electrodes; cleaning supplies; and the like. A customer can visit a walk-up service center, for example, to have a home dialysis machine serviced or to order supplies, and can use a centralized system at the walk-up service center to order and have shipped a repaired or serviced home dialysis machine, components for a home dialysis machine, a peripheral for a home dialysis machine, parts and/or supplies for a home dialysis machine, disposables for a home dialysis machine, consumables for a home dialysis machine, or a combination thereof, directly to the customer's home. For example, a customer can bring a home dialysis machine into, or send a home dialysis machine to, a walk-up service center for a diagnosis, then, using the centralized system, the customer and/or an employee or other representative of the walk-up service center can order the repaired or serviced machine, parts for the machine, and/or supplies or disposables for the machine, to be directly sent to the customer's home after the diagnosis. Ordering delivery of the serviced machine, parts for the machine, supplies for the machine, disposables for the machine, or a combination thereof can be enabled by an app, for example, an app on a smart phone, a smart watch, a tablet, a computer, a telephone, a web browser, or the like, that belongs to the customer or that is provided for use by the walk-up service center.

The home computer can include a processor, a memory, a user interface, and a data transmitter and receiver pair that transmits and receives data wired or wirelessly and can connect with the Internet, a wired network, a wireless network, a combination thereof, or the like. A software interface, such as a software program, a website, an app, or the like, can be loaded on the home computer. For example, the home computer can be a desktop, a laptop, a mobile computer, or the like, and a software program that interfaces with the one or more walk-up service centers can be loaded on the desktop, the laptop, the mobile computer, or the like. The home computer can be a portable computer, a smart phone, a tablet, a smart watch, a smart headset, a wearable device, an implantable device, a combination thereof, or the like. An app that interfaces with the one or more walk-up service centers can be loaded on the home computer. Additionally, a website that interfaces with the one or more walk-up service centers can be accessed by a web browser on or via the desktop, the laptop, or the mobile computer.

The software interface facilitates communication between a patient or caregiver of the home dialysis machine and the one or more walk-up service centers. For example, the patient or caregiver can schedule appointments with the one or more walk-up service centers such as for cleanings, services, maintenances, repairs, programming, or a combination thereof. The patient or caregiver can request new prescriptions, request consumable supplies for the home dialysis machine, or both using the software interface. The software interface can provide tracking information regarding the repair process of the home dialysis machine and provide estimated times for pick-up, delivery, shipping, and the like. An estimated time of arrival can be provided. The software interface can track a location of the home dialysis machine if the home dialysis machine is sent away from the walk-up service center for repair.

In an exemplary embodiment, the software interface can provide a geographical map showing a live location of the home dialysis machine. The software interface can provide estimated times of arrival for deliveries of new home dialysis machines, loaner dialysis machines, replacement parts, peripheral parts, prescriptions, consumable supplies, or the like. The deliveries can be to a walk-up service center, for the patient, are partner, or caregiver, to pick up. The deliveries can be deliveries directly to the home of a patient. The software interface can be an app. The software interface can be configured to order delivery of a serviced machine, order parts for the machine, order supplies for the machine, order disposables for the machine, or a combination thereof. The ordering can be enabled by an app, for example, an app on a smart phone, a smart watch, a tablet, a computer, a telephone, a web browser, or the like, that belongs to the customer or that is provided for use by the walk-up service center. The software interface or app can interface with a centralized ordering and shipping center at one or walk-up service centers. The app can show a user where a machine part, disposable, or consumable is physically located, show the closest available location for a machine part, disposable, or consumable, and can provide directions to that location. Specific delivery times or time frames can be arranged or specified by the software interface or app.

The software interface can also facilitate diagnostics of the home dialysis machine. A patient, care partner, or caregiver can report a problem of the home dialysis machine, via a software interface, by one or more of (1) selecting a general error prompt on the software interface, (2) selecting a problem from a list of common problems displayed by the software interface, (3) entering a specific text message or voice message describing the problem, (4) a combination thereof, (5) or the like. The software interface can prompt the patient, care partner, or caregiver to answer one or more questions to provide additional information. The information may regard problems of the home dialysis machine. The information can further prompt the patient, care partner, or caregiver to upload pictures or audio recordings of the home dialysis machine, for further diagnostics.

If it is determined that the home dialysis needs to be repaired, maintenance, exchanged, and/or cleaned at a walk-up service center, the software interface can prompt the patient, care partner, or caregiver, to schedule an appointment and to confirm the appointment. The software interface can further remind the patient, care partner, or caregiver of the time and date of the appointment.

The home dialysis machine network can include at least one walk-up service center that is equipped with a personnel consultation feature configured to provide a meeting place for a patient, care partner, or caregiver of the home dialysis machine to consult with personnel familiar with at least one of maintenance, service, cleaning, repair, and use of the home dialysis machine. The personnel consultation feature can comprise an in-person consultation at the walk-up service center and can include at least one of a chair, a desk, a table, a counter, and a window. The personnel consultation feature can further include remote consultations via live video and audio conferencing over the Internet or other wireless communication. The personnel consultation feature can comprise a personnel computer at the walk-up service center or at a home of a personnel that is in communication with the home computer of the patient or caregiver, in which personnel consultations are conducted remotely.

The network can include at least one walk-up service center that is located inside of a pharmacy store, drugstore, grocery store, a department store, and/or a shopping center. At least one walk-up service center can be located inside of a medical treatment facility. For example, the network can include a walk-up service center located inside of a doctor's office, inside of a dialysis treatment clinic, or the like. The home dialysis machine network can comprise one or more walk-up service centers that comprise a help desk and a waiting area.

The walk-up service center can be equipped with components of a home dialysis machine or a peripheral device to be used with the home dialysis machine, for example, equipped with a wearable device, a weighing scale, a blood pressure monitor, a body composition monitor, a body composition monitor diagnostic kit, a tubing set, a blood oxygen monitor, a pulse oximeter, a heart rate monitor, a blood potassium monitor, a blood potassium diagnostic kit, a body electrode, or a combination thereof. The component or peripheral device can be for sale, for rent, for lease, for loan, and/or for use.

The home dialysis machine can comprise a processor, a transmitter, and a receiver. At least one walk-up service center of the network can comprise a diagnostic tool configured to diagnose the home dialysis machine. The diagnostic tool can comprise a receiver configured to receive a status signal from a home dialysis machine, and the processor of the home dialysis machine can be configured to send, via the transmitter, a status signal pertaining to a status of the home dialysis machine. The status signal can be sent to the receiver of the diagnostic tool. The diagnostic tool can diagnose the home dialysis machine based on a status signal received, for example, the tool can identify at least one issue or component that is causing the machine or treatment to run with sub-optimal performance or to not run at all. The diagnostic tool can be programmed to run a second diagnostic step, selected from a plurality of possible diagnostic steps, in response to results obtained from a first diagnostic step.

The status signal can comprise an error code that is or had been generated by the home dialysis machine. The error code can include data pertaining to a warning such as fault encountered during operation of the home dialysis machine. The error code can comprise data pertaining to at least one of an expiration date, an elapsed time, a scheduled maintenance event, a parts authentication failure, a faulty component, a warn-out component, a non-licensed component, a non-licensed supply, an outdated software warning, a lock-out event, a pressure reading, a trans-membrane pressure reading, a kinked or clogged tubing, a fluid level value, a fluid level warning, or the like. The diagnosis can comprise comparing values received or measured, for example, pressures, flow rates, conductivities, and the like, and comparing such values to threshold values, value ranges, minimum values, maximum values, combinations thereof, or the like. The diagnosis can comprise reviewing stored events-history data. The diagnosis can comprise comparing received or measured values to values stored in a local memory, stored in a look-up table, obtained from a website, or the like. The diagnostic tool can comprise a display configured to display the status signal as an icon, a text, an audible signal, an alarm, a set of recommended instructions, a set of mandatory instructions, a combination thereof, or the like.

The transmitter of the home dialysis machine can comprise a first port, and the receiver of the diagnostic tool can comprise a second port. The network can be configured to transmit data from the home dialysis machine to the diagnostic tool through a wired connection between the first port and the second port. The home dialysis machine and the diagnostic tool can connect through a wireless connection.

The home computer can also be wirelessly paired with the home dialysis machine via a wireless connection, such as the Internet, WIFI, BLUETOOTH, or the like. The home computer can continuously receive status signals from the home dialysis machine and the software interface can act as a diagnostic tool. Alternatively, the status signals can be sent from the home computer to a remote diagnostic tool at the walk-up service center. The status signal can comprise the error code that had been generated by the home dialysis machine. If necessary, the software interface can then prompt a user to schedule an appointment with the walk-up service center.

At least one walk-up service center of the network can comprise a pharmacy. The pharmacy can comprise at least one of dialysate, concentrated dialysate, powdered dialysate, and packets of electrolytes formulated to mix with water to form dialysate. The pharmacy can comprise a prescription verification system configured to verify a prescription for dialysate to be used with the home dialysis machine. The pharmacy can comprise a prescription delivery system configured to deliver a prescription for dialysate to a user for whom the prescription for dialysate has been prescribed. At least one of the network walk-up service centers can comprise a doctor interface configured to enable a user to interface with a doctor and receive a prescription for dialysate. The processor of the home dialysis machine can be configured to generate a patient information signal pertaining to one or more patient parameters resulting from a treatment of a patient with the home dialysis machine. The doctor interface can comprise a physician computer processor, the prescription verification system can comprise a pharmacy computer processor, and the transmitter of the home dialysis machine or the home computer can be configured to wirelessly transmit a patient information signal to the physician computer processor. The physician computer processor can comprise a receiver for receiving the patient information signal, and a transmitter for transmitting prescription information that is based on the patient information signal. The pharmacy computer processor can comprise a receiver for receiving the prescription information. The doctor interface can comprise an interface transmitter that is configured to transmit a prescription for dialysate prescribed to the user, to the pharmacy. The doctor interface can comprise a doctor's chair, a doctor, a nurse, an administrator, or a combination thereof. The prescription verification system can comprise a computer, a pharmacist, or both.

The home dialysis machine network can further comprise a scheduling system. The scheduling system can comprise a telephone line, the software interface, or a combination thereof, on which an appointment can be scheduled. The appointment can be, for example, for: (i) repairing or servicing the home dialysis machine, a component of the home dialysis machine, a peripheral device to be used with the home dialysis machine, or a combination thereof; and/or (ii) engagement with a doctor, a pharmacist, a nurse, a home dialysis patient caregiver, a clinician, a technician, or a combination thereof. The scheduling system can be configured to schedule an appointment at one of the network walk-up service centers. The scheduling system can be configured to schedule an appointment at a home or other residence of a user of the home dialysis machine. The scheduling system can be automated such that a user is prompted to enter information via telephone or internet to schedule an appointment, without the need for human intervention with the user.

The network can comprise a pharmacy and the pharmacy can comprise a pharmacy processor. The pharmacy processor can be configured to: compare different prescribable consumables, compare deductible amounts for each of the different prescribable consumables, and compare reimbursable amounts the pharmacy receives for each of the different prescribable consumables. Based on the comparisons made, the pharmacy processor can determine and display the prescribable consumable that provides the highest cost/benefit ratio for the pharmacy, the greatest savings for the patient, or both. The pharmacy processor can be configured to diagnose information pertaining to a patient, for example, configured to evaluate physiological data about the patient, recommend a consumable for the patient, or both. The pharmacy processor can compare physical properties of different consumables, evaluate physiological data about the patient, and recommend a specific consumable for the patient based on the comparison and evaluation. The pharmacy processor can be configured to determine appropriate interventions that can be used, based on the diagnosis. The diagnosis can comprise comparing measured properties, for example, pressure and flow measurements, of the home dialysis machine with properties stored in a memory, and make recommendations for consumables, setting, or both. The memory can be part of the pharmacy processor. The pharmacy processor can be configured to recommend product and service proposals, based on the diagnosis. The pharmacy processor can be configured to recommend insurance policies, based on product and service proposals recommended. The pharmacy processor can communicate with the home computer to provide the above-mentioned information.

The diagnostic tool can comprise a processor and can be configured to provide a course-of-action signal comprising instructions to be carried out in maintenance of the home dialysis machine. The course-of-action signal can be based on a status signal received from the home dialysis machine or the home computer. The course-of-action signal can comprise mandatory instructions. The receiver of the home dialysis machine can be configured to receive the mandatory instructions and the home dialysis machine can be configured to prevent a treatment with or operation of the home dialysis machine until the mandatory instructions have been carried out. The home computer can be configured to receive the mandatory instructions on the software interface and the home computer can notify the user when the mandatory instructions have been received. The mandatory instructions can be displayed on a display or played on a speaker of the home computer.

The present invention also provides a method of maintaining a home dialysis machine, for example, a home dialysis machine of a network as described herein. The method can comprise transmitting a status signal pertaining to the status of the machine, to a diagnostic tool. The method can comprise generating a course-of-action signal with the diagnostic tool. The course-of-action signal can comprise instructions to be carried out in maintenance of the home dialysis machine. The method can involve generating a course-of-action signal based on a status signal received from the home dialysis machine. The method can comprise carrying out a course of action at, at least one of the one or more walk-up service centers, based on the course-of-action signal. The method can further involve displaying course-of-action instructions that are generated based on the course-of-action signal. At least one of the walk-up service centers can comprise a walk-up service center display, and the method can comprise displaying the course-of-action instructions on the walk-up service center display. The home computer can be configured to receive the course-of-action instructions on the software interface and the home computer can notify the user when the course-of-action instructions have been received. The course-of-action instructions can be displayed on a display or played on a speaker of the home computer. The course-of-action instructions can include instructions to clean the home dialysis machine. The method can further comprise cleaning the home dialysis machine at, at least one of the one or more walk-up service centers or at the user's home. The method can involve generating a course-of-action instruction that includes instructions to replace the home dialysis machine, a component of the home dialysis machine, a peripheral device to be used with the home dialysis machine, or a combination thereof. The method can further comprise replacing the home dialysis machine, a component of the home dialysis machine, a peripheral device to be used with the home dialysis machine, or a combination thereof. The replacing can be performed at, at least one of the one or more walk-up service centers. Instructions can be sent to the home dialysis machine explaining how to perform a replacement at home. For example, the home computer can receive the instructions on the software interface. A component of the home dialysis machine, a peripheral device to be used with the home dialysis machine, or a combination thereof can be sent to the home. The patient or caregiver can follow the instructions on the home computer to perform the replacement.

The processor of the home dialysis machine can comprise a cache, and the processor can be configured to store event information in the cache. The method can comprise analyzing event information stored in the cache and generating a course-of-action signal based on the analysis of the event information. The course-of-action can comprise uploading a software update to the home dialysis machine and the method can comprise uploading the update. The course-of-action instructions can include instructions to input a prescription into the home dialysis machine, and the method can further comprise inputting the prescription into the home dialysis machine. The inputting can occur at the user's home or at, at least one of the one or more walk-up service centers. The home dialysis machine can be a lightweight machine, for example, weighing less than 25 pounds. The method can further comprise transporting the home dialysis machine from a patient's home to at least one of the one or more walk-up service centers.

The method can comprise transmitting a status signal pertaining to the home dialysis machine, to a desired one of the one or more walk-up service centers. The desired walk-up service center can comprise a center transmitter. The method can involve receiving, at the desired walk-up service center, the transmitted status signal, and determining, at the desired walk-up service center, whether a part for the home dialysis machine is needed. The determination can be made based on the transmitted status signal. The method can then comprise transmitting, via the center transmitter, a signal from the desired walk-up service center to the home dialysis machine or the home computer indicating that a part is needed and available. The method can instead comprise transmitting, via the center transmitter, a signal from the desired walk-up service center to the home dialysis machine or the home computer indicating that a part is needed, not available, but has been ordered. The method can instead comprise transmitting, via the center transmitter, a signal from the desired walk-up service center to the home dialysis machine or the home computer indicating that no part is needed. At least some of the transmitting from the home dialysis machine or the home computer to the desired walk-up service center can occur wirelessly and the transmitting can comprise directly transmitting or indirectly transmitting through one or more intermediate devices. The transmitting from the desired walk-up service center to the home dialysis machine or the home computer can occur wirelessly and the transmitting can comprise directly transmitting or indirectly transmitting through one or more intermediate devices.

The method can involve transmitting, via the center transmitter, a signal from the desired walk-up service center to the home dialysis machine or the home computer indicating that a part is needed and available. The method can involve transporting the home dialysis machine to the desired walk-up service center. The method can involve replacing the part at the desired walk-up service center. The method can further comprise transmitting a status signal pertaining to the home dialysis machine, to a desired one of the one or more walk-up service centers, wherein the desired walk-up service center further comprises a center transmitter. The method can then involve receiving, at the desired walk-up service center, the transmitted status signal. The method can involve then determining, at the desired walk-up service center, whether a software update is needed and available for the home dialysis machine. The method can then involve transmitting, via the center transmitter, a signal from the desired walk-up service center to the home dialysis machine or the home computer indicating whether a software update for the home dialysis machine is needed and available. The transmitting via the center transmitter can further comprise transmitting a signal that a software update for the home dialysis machine is needed and available, and transmitting the needed and available software update to the home dialysis machine.

Alternatively, when the home computer is paired with the home dialysis machine, the home computer can communicate with the home dialysis machine via the software interface to check whether a software update for the home dialysis machine is needed and update the home dialysis machine by uploading the software update to the home dialysis machine.

A network is also provided that comprises a home dialysis machine, the home computer, and the one or more walk-up service centers, wherein the home dialysis machine comprises a memory, a transmitter, and a control system. The control system, the home computer, or both can be configured to store in the memory treatment history information pertaining to treatments carried out on a patient using the home dialysis machine. The transmitter of the home dialysis machine or the home computer can be configured to wirelessly transmit the treatment history information to at least one of the one or more walk-up service centers, and the at least one walk-up service center can comprise a receiver for receiving the treatment history information. The home dialysis machine of the network can comprise a unique identifier, and the one or more walk-up service centers can comprise an integrated system configured to identify the home dialysis machine by reading the unique identifier of the home dialysis machine. The integrated system can be configured to match the unique identifier of the home dialysis machine with warranty information to determine whether the home dialysis machine is under a warranty. The unique identifier can comprise a data storage device, and the control system can be configured to store, in the data storage device, maintenance and repair history information pertaining to a history of maintenance and repair procedures that have been performed, or need to be performed, on the home dialysis machine.

A method is also provided for reporting treatment history information to at least one of the one or more walk-up service centers of the network. The method can comprise transmitting treatment history information from the transmitter of the home dialysis machine or the home computer to a desired one of the one or more walk-up service centers. At least some of the transmitting can occur wirelessly and the transmitting can comprise directly transmitting or indirectly transmitting data through one or more intermediate devices. The method can involve receiving, at the desired walk-up service center, the transmitted treatment history information. The method can involve transmitting, from the walk-up service center, course-of-action instructions to the home dialysis machine or the home computer. The course-of-action instructions transmitted can include instructions to transport the home dialysis machine to at least one of the walk-up service centers for cleaning, service, maintenance, repair, programming, or a combination thereof.

A method of educating a home dialysis patient or a home dialysis patient caregiver is also provided. The educating can be carried out at a home dialysis machine walk-up service center or at home via the home computer. For example, the method of educating can take place via live video and audio conferencing over the Internet or other wireless communication. The method of educating can include an educator computer at the walk-up service center or at a home of an educator that is in communication with the home computer via the software interface, in which the education is conducted remotely. The method can comprise demonstrating a home dialysis product to a home dialysis patient, to a home dialysis patient caregiver, or to both, wherein the demonstrating can be performed by a nephrologist, clinician, technician, dietician, or nutritionist, at the home dialysis machine walk-up service center. The method can comprise presenting a nutritional seminar to a home dialysis patient, to a home dialysis patient caregiver, or to both, and the presenting can be performed by a nephrologist, clinician, technician, dietician, or nutritionist, at the home dialysis machine walk-up service center. The method can comprise explaining an organ transplant procedure to a home dialysis patient, to a home dialysis patient caregiver, or to both, and the explaining can be performed by a nephrologist, clinician, technician, nurse, doctor, or surgeon, at the home dialysis machine walk-up service center. The method can comprise assisting a home dialysis patient, a home dialysis patient caregiver, or both, with obtaining insurance benefits, and the assisting can be performed by a clinician, technician, social service worker, nurse, or insurance agent, at the home dialysis machine walk-up service center or at home via the home computer. The method can comprise advising a home dialysis patient, a home dialysis patient caregiver, or both, on how to perform a dialysis treatment, and the advising can be performed by a nephrologist, clinician, technician, nurse, or doctor, at the home dialysis machine walk-up service center or at home via the home computer.

The method can further comprise transporting a home dialysis patient to or from the home dialysis machine walk-up service center. The one or more home dialysis machine walk-up service centers can comprise one or more local home dialysis machine walk-up service centers. Each local home dialysis machine walk-up service center can be equipped with a diagnostic tool configured to diagnose a home dialysis machine, a component of a home dialysis machine, a peripheral device to be used with a home dialysis machine, or a combination thereof. The diagnostic tool can diagnose by receiving or measuring values, for example, measured pressures, flow rates, conductivities, and the like, and comparing such values to threshold values, value ranges, minimum values, maximum values, combinations thereof, or the like. The diagnostic tool can diagnose by comparing received or measured values to values stored in a local memory, values stored in a look-up table, values obtained from a website, values obtained from a physical table or chart, or the like. Each local home dialysis machine walk-up service center can be equipped with parts for servicing, repairing, or both, a home dialysis machine, a component of a home dialysis machine, a peripheral device to be used with a home dialysis machine, or a combination thereof. Each local home dialysis machine walk-up service center can be equipped with supplies to be consumed before, during, or subsequent to operation of a home dialysis machine.

Each local home dialysis machine walk-up service center can also be equipped with at least one of a gymnasium, a spa, a lounge, one or more dialysis-treatment rooms comprising a dialysis machine configured for treatment of a patient, one or more conference rooms, one or more stations stocked with food and fluids for dialysis treatment patients, and one or more kiosks. The home dialysis machine walk-up service center can comprise one or more conference rooms. At least one conference room can comprise a computing device and a screen configured to demonstrate new products to a home dialysis patient, a home dialysis patient caregiver, or both. The home dialysis machine walk-up service center can comprise at least one conference room that includes a display configured to demonstrate new therapies to a home dialysis patient, a home dialysis patient caregiver, or both. The home dialysis machine walk-up service center can comprise one or more conference rooms that includes a computing device and a screen configured to present a seminar on a new home dialysis technology, a surgical technology, or both, and the seminar can be presented to a home dialysis patient, a home dialysis patient caregiver, or both. The home dialysis machine walk-up service center can comprise at least one conference room that includes educational materials configured to provide nutritional information to a home dialysis patient, a home dialysis patient caregiver, or both. The home dialysis machine walk-up service center can comprise at least one conference room that includes educational materials configured to provide organ transplant consultation to a home dialysis patient, a home dialysis patient caregiver, or both. The home dialysis machine walk-up service center can comprise at least one conference room that includes educational materials configured to provide insurance assistance to a home dialysis patient, a home dialysis patient caregiver, or both. The home dialysis machine walk-up service center can comprise at least one conference room that includes educational materials configured to provide mental health treatment education to a home dialysis patient, a home dialysis patient caregiver, or both.

The home dialysis machine walk-up service center can comprise a gymnasium. The gymnasium can comprise a mirror, a programmable treadmill, a programmable rowing machine, a programmable exercise machine having pedals, a treadmill, a rowing machine, an exercise machine having pedals, an exercise bicycle, a weight-lifting set, a sauna, a hot tub, a Jacuzzi, or the like. The home dialysis machine walk-up service center can comprise a repair workshop. The repair workshop can comprise a workbench and tools. The tools can be configured for servicing a home dialysis machine.

The home dialysis machine walk-up service center can comprise a video conferencing center. The video conferencing center can be networked to a nephrologist's office and can be configured to enable video conferencing with a nephrologist. The home dialysis machine walk-up service center can further comprise a theatre and theatre seating, to enable a person to view a movie or other entertainment while waiting for a home dialysis machine to be analyzed, serviced, maintained, repaired, replaced, programmed, updated, or a combination thereof. The home dialysis machine walk-up service center can further comprise a tour vehicle programmed to ferry persons away from a home dialysis machine service center, to a home dialysis service center, or both. The tour vehicle can comprise an autonomous vehicle control system. The tour vehicle can comprise a built-in dialysis machine.

The home dialysis machine walk-up service center can comprise one or more kiosks, and at least one of the kiosks can comprise a display unit including a display screen. At least one kiosk can comprise a demonstration including a home dialysis machine, a component of a home dialysis machine, or both.

The home dialysis machine walk-up service center can comprise at least one local home dialysis machine walk-up service center that includes a reader. The reader can be configured to read a machine identifier located on or in a home dialysis machine. The reader can be configured to read a machine identifier located on or in a component of a home dialysis machine. The reader can be configured to read a machine identifier located on or in a peripheral device to be used with a home dialysis machine. The reader can comprise a radio frequency identification (RFID) reader, a bar code reader, a two-dimensional bar code reader, a scanner, or the like. The local home dialysis machine walk-up service center can further comprise a processor programmed to compare a read machine identifier, read by the reader, to information pertaining to a warranty, a recall, a notice, repair or maintenance history, a combination thereof, or the like. The local home dialysis machine walk-up service center can comprise a diagnostic tool that comprises a processor and an input unit, wherein the processor can be programmed with predictive analytics software that recommends a suggested course of action based on symptom information inputted into the input unit. A method is provided that involves inputting symptom information into the input unit of the diagnostic tool, processing the information inputted, using the predictive analytics software, and recommending a suggested course of action based on the processing. The method can further comprise carrying out the suggested course of action.

The home dialysis machine walk-up service center can comprise a diagnostic tool that comprises an artificial intelligence (AI) system. The AI system can be programmed to use information attained from the diagnostic tool to build a database and learn how to best predict a necessary course of action in order to service a home dialysis machine diagnosed by the diagnostic tool. The diagnosis can comprise the AI system identifying at least one issue or component that is causing the machine or treatment to run with sub-optimal performance, or not at all. The AI system can be programmed with a learning intake assessment program that triages service issues related to the home dialysis machine, either remotely or at the home dialysis machine walk-up service center. The AI system can learn from past diagnoses and be better and better equipped to more efficiently and rapidly diagnose a home dialysis machine, over time. The AI system can choose a second diagnostic step in response to results obtained from a first diagnostic step.

The home dialysis machine walk-up service center network can further comprise a robot at one or more local home dialysis machine walk-up service centers. The robot can be configured with an artificial intelligence (AI) system and can be configured to assist a home dialysis patient, a home dialysis patient caregiver, a service provider, or a combination thereof, with a method performed at one or more of the local home dialysis machine walk-up service centers. The method that the robot can be configured to assist with can comprise demonstrating a home dialysis product to a home dialysis patient, to a home dialysis patient caregiver, or to both, the demonstrating being performed by a nephrologist, clinician, technician, dietician, or nutritionist, at the home dialysis machine walk-up service center. The method that the robot can be configured to assist with can comprise presenting a nutritional seminar to a home dialysis patient, to a home dialysis patient caregiver, or to both, the presenting being performed by a nephrologist, clinician, technician, dietician, or nutritionist, at the home dialysis machine walk-up service center. The method that the robot can be configured to assist with can comprise explaining an organ transplant procedure to a home dialysis patient, to a home dialysis patient caregiver, or to both, the explaining being performed by a nephrologist, clinician, nurse, doctor, or surgeon, at the home dialysis machine walk-up service center. The method that the robot can be configured to assist with can comprise assisting a home dialysis patient, a home dialysis patient caregiver, or both, with obtaining insurance benefits, the assisting being performed by a clinician, technician, social service worker, nurse, or insurance agent, at the home dialysis machine walk-up service center. The method that the robot can be configured to assist with can comprise advising a home dialysis patient, a home dialysis patient caregiver, or both, on how to perform a dialysis treatment, the advising being performed by a nephrologist, clinician, technician, nurse, or doctor, at the home dialysis machine walk-up service center.

The home dialysis machine walk-up service center can further be equipped with a contactless service feature that can be implemented via an app loaded on the mobile computer, or via the website accessed via a web browser on a mobile computer. The contactless service feature can be used to prevent exposure of a patient, care partner, or caregiver, to an environment conducive to contracting diseases, such as COVID-19 infections, for example, viral or bacterial infections. The app enables a patient, care partner, or caregiver to communicate with a home dialysis machine walk-up service center, doctor, clinician, technician, physician, repair expert, or the like, for the purpose of facilitating a repair, maintenance, exchange, cleaning, or other servicing of the home dialysis machine, particularly via a contact-free procedure. Using the contactless service feature, a patient, care partner, or caregiver can report a problem concerning the home dialysis machine, and the reporting can be via prompts, text messages, voice messages, combinations thereof, and the like. Notifications can be sent via the contactless service feature, for example, letting a customer know that a software update is available or a recall notice has been issued.

The app can be configured to provide a patient, care partner, caregiver, or other customer with updates, upgrades, and patches for software, firmware, hardware, or combinations thereof pertaining to, run by, or stored on a home dialysis machine, a peripheral therefor, the network, or the like. The app can be configured to notify a patient, care partner, caregiver, or other customer that an update, upgrade, or patch I available for software, firmware, hardware, or combinations thereof pertaining to, run by, or stored on a home dialysis machine, a peripheral therefor, the network, or the like. The app can specify between a mandatory update, a recommended update, an optional update, and the like.

As an example, the app can prompt the patient, care partner, or caregiver to answer questions and/or to provide additional information regarding the problems of or with the home dialysis machine. The app can prompt the patient, care partner, or caregiver to upload pictures or audio recordings of the home dialysis machine, for further diagnostics. If it is determined that the home dialysis machine needs to be repaired, maintained, exchanged, and/or cleaned, at a walk-up service center, the app can prompt the patient, care partner, or caregiver to schedule an appointment. On the appointment day, the patient, care partner, or caregiver can drive to the walk-up service center. The app can track the person or automobile, notify the walk-up service center when the person has arrived at the walk-up service center, or notify the walk-up service center through the app or through another form of communication (e.g., via telephone), that the person has arrived at the walk-up service center. Personnel of the walk-up service center can meet the patient, care partner, or caregiver outside of the walk-up service center, such as at the car or transport vehicle of the patient, care partner, or caregiver. Thus, a convenient, contactless, pick-up, drop-off, exchange, or the like, of a home dialysis machine, a loaner dialysis machine, a component of a home dialysis machine, a peripheral device to be used with a home dialysis machine, or a combination thereof, can be carried out. The app can provide curb-side delivery of prescriptions, consumables, other supplies, and the like. The app can provide links to software updates, tracking status for shipping orders, and the like.

The home dialysis machine can have a user interface and a patient can use the user interface to send and receive information, instructions, and software. The user interface can include an apparatus for entering information, such as a touchscreen or keypad. The user interface can be used for transmitting information to the user, and can include, for example, a monitor, a display screen, an LCD display, a speaker, a vibrating alarm, or the like. The user interface can be paired or otherwise integrated with the home computer, such a smart phone, a tablet, a smart watch, a smart headset, a wearable device, an implantable device, a desktop, a laptop, and the like. The user interface assembly can be in continuous or intermittent data communication with the home dialysis machine, for example, via wireless radio frequency transmission (for example, via LF, RF, or standard wireless protocols such as BLUETOOTH), but could instead or also be connected via data cable, optical connection, or by another suitable data connection. The user interface can communicate with a processor to input parameters or other data and to receive status and function updates such as the presence of any error conditions, a need for maintenance, the passage of an expiration date, the amount of a prescription remaining, the presence of an unauthorized disposable component, or the like. The interface can transmit error signals to a walk-up service center, to a doctor, to a patient's guardian or medical professional, or to the patient. The transmission can be made through a telephone, email, pager, instant messaging, or other suitable communication device or medium.

FIG. 1 is a flow diagram showing the various steps and orders that are followed according to an exemplary method carried out by a home dialysis machine network according to an exemplary embodiment of the present invention. As shown in FIG. 1, a home dialysis machine transmits prescription and treatment details to a walk-up service center. The center alerts a physician when needed, to request a renewed or new prescription or instructions for the patient and the patient's home dialysis treatment. The physician sends a new prescription, new treatment instructions, or both, to the home dialysis machine. The home dialysis machine then administers the dialysis treatment to the patient. In some cases, wherein physician interaction is not necessary, for example, a service reminder or cleaning instructions, the walk-up service center can send instructions directly to the home dialysis machine, patient, or both. Prescriptions filled and instructions provided by the pharmacy system can be sent directly to the patient or to the walk-up service center. An app can provide many of the same services as the service center. a home dialysis machine transmits prescription and treatment details to a walk-up service center. The app can alert a physician when needed, to request a renewed or new prescription or instructions for the patient and the patient's home dialysis treatment. The physician can send a new prescription, new treatment instructions, or both, to the app. The app can then communicate with the home dialysis machine to administer the dialysis treatment to the patient. In some cases, wherein physician interaction is not necessary, for example, a service reminder or cleaning instructions, the app can send instructions directly to the home dialysis machine, patient, or both. Notifications regarding prescriptions filled and instructions provided by the pharmacy system can be sent directly to the patient or to the walk-up service center, through the app.

Figure 2:
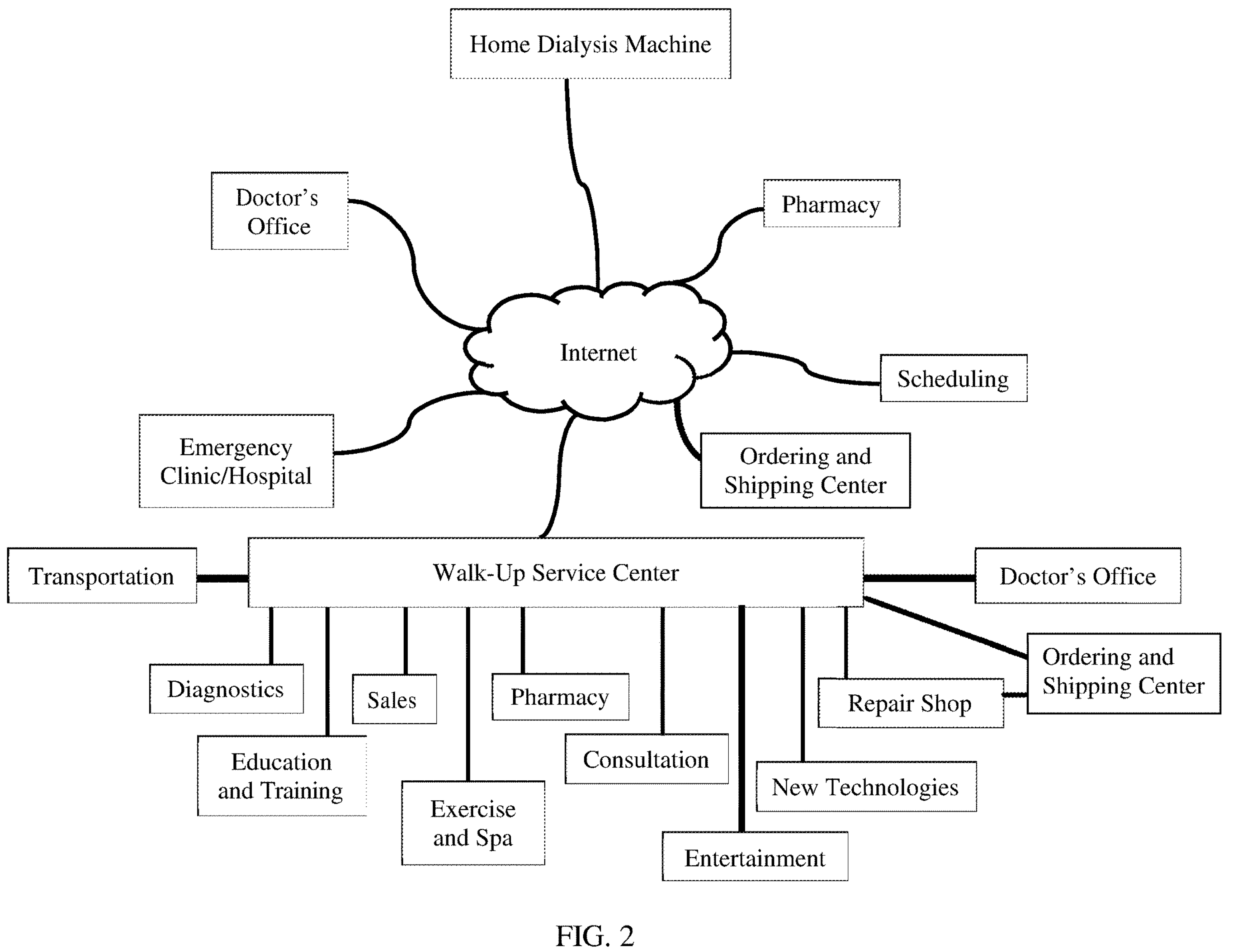
FIG. 2 is a schematic diagram showing various physical spaces, offices, and departments that are connected together, physically and/or through the internet, that make-up a home dialysis machine network according to an exemplary embodiment of the present invention.

FIG. 2 is a schematic diagram showing the various physical or virtual spaces connected together, physically and/or through the internet, that make-up a home dialysis machine network according to an exemplary embodiment of the present invention. As shown in FIG. 2, a home dialysis machine is linked to a walk-up service center, a doctor's office, a pharmacy, a scheduling service, and a clinic or hospital, through the internet and wireless, cloud-based computing and communication. The walk-up service center is equipped with a number of features, as described herein, including a transportation service or office, a diagnostics department, an education and training department, a consultation department, an exercise and spa department, an entertainment department, a sales department, a repair shop, an ordering and shipping center, a new technologies department, a pharmacy, and a doctor's office. Each of the doctor's office and the pharmacy that are physically connected to and part of the walk-up service center can replace the separate doctor's office and pharmacy that are linked to the network only through the internet. Alternatively, the walk-up service center can be free of a doctor's office, pharmacy, ordering and shipping center, or a combination thereof, if such locations are made available through internet connections at remote locations.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such a range is separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All patents, patent applications, and publications mentioned herein are incorporated herein in their entireties, by reference, unless indicated otherwise.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A home dialysis machine system network comprising a home dialysis machine, and one or more walk-up service centers, wherein at least one of the one or more walk-up service centers comprises a pharmacy and the pharmacy comprises at least one of dialysate, concentrated dialysate, powdered dialysate, and packets of electrolytes formulated to mix with water to form dialysate, a prescription verification system comprising a pharmacy computer processor that comprises a receiver, and a prescription delivery system to deliver the prescription for dialysate to a user for whom the prescription for dialysate has been prescribed;

the at least one of the one or more walk-up service centers comprises an interface that comprises a physician computer processor;

the home dialysis machine comprises a processor, a transmitter, and a receiver;

the processor of the home dialysis machine is configured to generate a patient information signal pertaining to one or more patient parameters resulting from a treatment of a patient with the home dialysis machine;

the transmitter of the home dialysis machine is configured to wirelessly transmit the patient information signal to the physician computer processor;

the physician computer processor comprises a receiver for receiving the patient information signal and a transmitter for transmitting a prescription for dialysate to be used with the home dialysis machine, the prescription being based on the patient information signal, to the pharmacy computer processor;

the receiver of the pharmacy computer processor is configured for receiving the prescription from the physician computer processor, the pharmacy computer processor is configured to verify the prescription, the interface is configured to enable a user to receive the prescription for dialysate to be used with the home dialysis machine, and the processor of the home dialysis machine is configured to generate course-of-action instructions to input the prescription into the home dialysis machine.

2. The home dialysis machine network of claim 1, wherein:

at least one of the one or more walk-up service centers is equipped with a personnel consultation feature configured to provide a meeting place for (i) a patient that uses the home dialysis machine, (ii) a care partner of the patient, or (iii) a caregiver of the patient, to consult with personnel familiar with at least one of maintenance, service, cleaning, repair, and use of the home dialysis machine; and the personnel consultation feature comprises at least one of a chair, a desk, a table, a counter, and a window.

3. The home dialysis machine network of claim 2, wherein the personnel consultation feature is equipped for remote consultations via live video and audio conferencing over the Internet and/or using wireless communication.

4. The home dialysis machine network of claim 2, wherein the personnel consultation feature comprises a personnel computer that is in communication with a home computer of (i) the patient, (ii) the care partner of the patient, or (iii) the caregiver of the patient, and the personnel computer and the home computer are configured to remotely conduct personnel consultations.

5. The home dialysis machine network of claim 1, wherein at least one of the one or more walk-up service centers comprises one or more of a transportation service office, a diagnostics department, and an education and training department.

6. The home dialysis machine network of claim 1, wherein at least one of the one or more walk-up service centers comprises at least one of a gymnasium, a spa, a lounge, one or more dialysis-treatment rooms comprising a dialysis machine configured for treatment of a patient, one or more conference rooms, one or more stations stocked with food and fluids for dialysis treatment patients, and one or more kiosks.

7. The home dialysis machine network of claim 2, wherein the personnel consultation feature is part of a consultation department, and the at least one walk-up service center equipped with the personnel consultation feature also comprises one or more of a transportation service department, a diagnostics department, an education department, a training department, an exercise department, a spa department, an entertainment department, a sales department, a repair shop, a new technologies department, a pharmacy, and a doctor's office.

8. The home dialysis machine network of claim 2, wherein the at least one walk-up service center equipped with the personnel consultation feature also comprises a diagnostics department, and a repair shop.

9. The home dialysis machine network of claim 2, wherein the at least one walk-up service center equipped with the personnel consultation feature is located in an existing pharmacy store, an existing drug store, an existing grocery store, or an existing department store.

10. The home dialysis machine network of claim 1, wherein the pharmacy computer processor is configured to:

compare different prescribable consumables, deductible amounts for each of the different prescribable consumables, and reimbursable amounts the pharmacy receives for each of the different prescribable consumables; and based on the comparisons made, determine and display the prescribable consumable that provides the highest cost/benefit ratio for the pharmacy.

11. The home dialysis machine network of claim 1, wherein the pharmacy computer processor is configured to:

diagnose information pertaining to a patient;

determine appropriate interventions that can be used, based on the diagnosis;

recommend product and service proposals, based on the diagnosis; and recommend insurance policies, based on the product and service proposals recommended.

12. The home dialysis machine network of claim 1, wherein at least one of the one or more walk-up service centers is equipped with (i) a diagnostic tool configured to diagnose the home dialysis machine, a component of the home dialysis machine, a peripheral device to be used with the home dialysis machine, or a combination thereof, (ii) parts for servicing, repairing, or both, the home dialysis machine, a component of the home dialysis machine, a peripheral device to be used with the home dialysis machine, or a combination thereof, and (iii) supplies to be consumed before, during, or subsequent to operation of the home dialysis machine; and at least one of the one or more walk-up service centers comprises a repair workshop comprising tools configured for servicing the home dialysis machine.

13. The home dialysis machine network of claim 12, wherein the diagnostic tool comprises an app downloaded on a remote device, the remote device being configured to execute the app to upload information to the one or more walk-up service centers, the information pertaining to at least one of maintenance of, service of, cleaning of, repair of, and use of the home dialysis machine.

14. The home dialysis machine network of claim 12, wherein the diagnostic tool comprises a processor and is configured to provide a course-of-action signal comprising instructions to be carried out in maintenance of the home dialysis machine, based on a status signal received from the home dialysis machine.

15. The home dialysis machine network of claim 14, wherein the course-of-action signal comprises mandatory instructions, the receiver of the home dialysis machine is configured to receive the mandatory instructions, and the home dialysis machine is configured to prevent treatment operation of the home dialysis machine until the mandatory instructions have been carried out.

16. The home dialysis machine network of claim 12, wherein the diagnostic tool comprises a processor and an input unit, the processor being programmed with predictive analytics software that recommends a suggested course of action based on symptom information inputted into the input unit.

17. The home dialysis machine network of claim 12, wherein the diagnostic tool comprises an artificial intelligence (AI) system, the AI system being programmed to use information attained from the diagnostic tool to build a database and learn how to best predict a necessary course of action in order to service a home dialysis machine diagnosed by the diagnostic tool.

18. The home dialysis machine system of claim 1, further comprising a diagnostic tool, wherein the processor of the home dialysis machine is configured to generate a status signal pertaining to the status of the home dialysis machine, the transmitter of the home dialysis machine is configured to transmit the status signal to the diagnostic tool, the diagnostic tool is configured to receive the status signal, the diagnostic tool comprises a processor that is configured to generate a course-of-action signal based on the status signal received, the course-of-action signal comprises mandatory instructions to be carried out in maintenance of the home dialysis machine, the receiver of the home dialysis machine is configured to receive the mandatory instructions, and the home dialysis machine is configured to prevent a treatment with, or operation of, the home dialysis machine until the mandatory instructions have been carried out.

* * * * *